United States Patent [19]

Pappenheimer et al.

[11] 4,342,748

[45] Aug. 3, 1982

[54] SLEEP-PROMOTING FACTOR

[75] Inventors: John R. Pappenheimer, Cambridge; James M. Krueger, Newton; Manfred L. Karnovsky, Cambridge, all of Mass.

[73] Assignee: President and Fellows of Harvard College, Cambridge, Mass.

[21] Appl. No.: 229,654

[22] Filed: Jan. 29, 1981

Related U.S. Application Data

[63] Continuation-in-part of Ser. No. 166,909, Jul. 8, 1980, abandoned, which is a continuation-in-part of Ser. No. 52,969, Jun. 28, 1979, abandoned, which is a continuation of Ser. No. 891,362, Mar. 29, 1978, abandoned.

[51] Int. Cl.³ .............................................. A61K 35/12
[52] U.S. Cl. ...................................................... 424/95
[58] Field of Search .......................................... 424/95

[56] References Cited

PUBLICATIONS

Federation Proceedings—vol. 40, May 11, 1981, pp. 273 and 274, abst. 213 and 220.
Krueger et al.—Am. J. Physiol., vol. 238, pp. E116–E123 (Feb. 1980).
Pappenheimer et al., J. Neurophysiology, 38, 1299–1311 (1975).
Chem. Abstr. 84: 102726t (1976).

Primary Examiner—Sam Rosen

[57] ABSTRACT

Sleep-promoting factor isolated from brains of sleep-deprived animals or from human urine and concentrated using ion-exchange resins.

7 Claims, No Drawings

SLEEP-PROMOTING FACTOR

The invention described herein was made in the course of work under grants and awards from the American Heart Association, from the Department of Health, Education, and Welfare, and from Office of Naval Research.

This application is a continuation-in-part of our co-pending application Ser. No. 166,909 filed July 8, 1980, which in turn is a continuation-in-part of our copending application Ser. No. 52,969 filed June 28, 1979, which in turn is a continuation of Ser. No. 891,362 filed Mar. 29, 1978, all now abandoned.

This invention is concerned with sleep-promoting Factor S, which is a low molecular weight substance found in the brain and cerebrospinal fluid of sleep-deprived animals and in the urine of humans. Infusion of Factor S into the cerebral ventricles of rats, cats and rabbits induces excess slow-wave sleep (SWS) in the recipients for several hours.

Partial purification of Factor S from cerebrospinal fluid and brains of sleep-deprived goats has been described by Pappenheimer et al., in *J. Neurophysiol.*, 38, 1299 (1975), but the quantity and purity of the product were inadequate to permit further studies.

Now with the present invention there is provided relatively pure Factor S, as well as processes for its isolation and purification both from the brains of sleep-deprived animals and from human urine. Factor S is a low molecular weight organic material: it passes through a molecular sieve (Diaflo UM 05), which prevents the passage of molecules larger than 1000 daltons. It elutes prior to sucrose on a polysaccharide gel filtration column (Sephadex G10), and has $R_f$ 0.15–0.35 after ascending development on Whatman No. 1 paper with a solvent system of acetone:1-propanol:water:8 M NH$_4$OH (40:30:20:10, V:V:V:V). It has $R_{LYS}$ 0.2–0.3 after high voltage electrophoresis at pH 1.9, 65 V cm$^{-1}$ for 60 minutes in formic acid:acetic acid:water (150:100:750, V:V:V) on Whatman No. 3 paper. Brain-derived Factor S is inactivated by incubation with carboxypeptidase, suggesting a peptide structure. Acid hydrolysis of Factor S releases muramic acid, alanine, diaminopimelic acid (DAP), and glutamic acid, in the molar ratio 1:2:1:2.

Factor S occurs in both a cationic and an anionic form, both of which forms occur in human urine. At least the cationic form occurs in rabbit brains. Upon elution from a cation exchange resin under acidic conditions, the cationic form exhibits the unusual characteristic of being converted to the anionic form. Intraventricular infusion of either form induces prolonged slow-wave sleep in animals.

Factor S does not react with fluorescamine and passes a Diaflo UM05 ultrafiltration membrane which retains molecules having a molecular weight greater than 1000 daltons.

Factor S induces normal sleep in animals, including primates. As applied to clinical medicine, it can be administered orally, rectally, intravenously, intramuscularly, or intraperitoneally in doses of 0.1 to 10 mg/kg/day.

It is to be noted that the precise unit dosage form and dosage level depend upon the case history of the individual being treated and, consequently, are left to the discretion of a skilled therapist.

Pharmaceutical compositions comprising a compound useful in the novel method of treatment as active ingredient may be in any art recognized form suitable for oral suspensions, dispersible powders, or granules, emulsions, hard or soft capsules, syrups, or elixirs. For intravenous and intramuscular and intraperitoneal use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 mg. to 500 mg.

The following specific examples are intended to more clearly point out the invention without acting as limitations upon its scope.

EXAMPLE 1

Preparation of Factor S from Brain Tissue

Step I: Extraction from Brain

Twenty-five kg. of brains from approximately 3000 sleep-deprived rabbits were homogenized to a uniform consistency in a Gilford wood colloid mill in a solution (a volume was used which was 5 times in liters the frozen weight of the tissue in kilograms) of acetone-1 N HCl (100:3, V/V). The mixture was stirred at 4° C. for 3 hours and then filtered by suction through Whatman No. 1 filter paper. The residue was re-extracted in a solution (a volume was used which was 2 times in liters the original frozen weight of the tissue in kilograms) of acetone 0.01 N HCl (80:20, V/V). The two filtrates were pooled and extracted five times with petroleum ether (b.p. 36°–50.9°). Each time a volume of petroleum ether was used which was one-fifth of the volume of the combined filtrates. The aqueous phase which contained all of the Factor S was reduced in volume by evaporation under low pressure at 38° C. to one-fifth of its volume. The resulting aqueous suspension was centrifuged at 14,000 g in a continuous flow centrifuge. The ionic strength of the supernate was adjusted to the equivalent of 0.15 M NaCl and titrated to pH 7.2 with NH$_4$OH. At this stage the concentration of the extract was 1.2 Gram Brain Equivalents (GBE) per ml. Since biological assays for Factor S are not sufficiently quantitative to establish a biological unit of activity concentrations and doses are expressed in terms of GBE of the original starting material.

Step II: Ion Exchange

The extract from Step I was applied to a carboxymethyl polysaccharide [(CM) Sephadex C-25] column equilibrated at room temperature with NH$_4$Ac buffer 50 mM, pH 7.2; the bed volume of the column was 6.6 ml/100 GBE. The column was then washed with 1 bed volume of 50 mM NH$_4$Ac buffer, pH 7; since Factor S is retained by the column under these conditions, the wash was discarded. Factor S was then eluted with concentrated HAC—HCOOH at pH 1.9, which treatment also converted the cationic form of Factor S to the anionic form. Buffers and other small molecules were then removed by gel-filtration on a Sephadex G10 column. The eluate was then applied to a DEAE anionic exchange column, and Factor S was eluted with 1 M NaCl, which was then removed by gel-filtration on a Sephadex G10 column.

Brain derived Factor S in an even more purified state could be obtained by using, after the extraction step, the purification procedure described below for urine-derived Factor S.

EXAMPLE 2

Preparation of Factor S from Human Urine

The flow chart below summarizes the steps by which Factor S was isolated and purified from human urine.

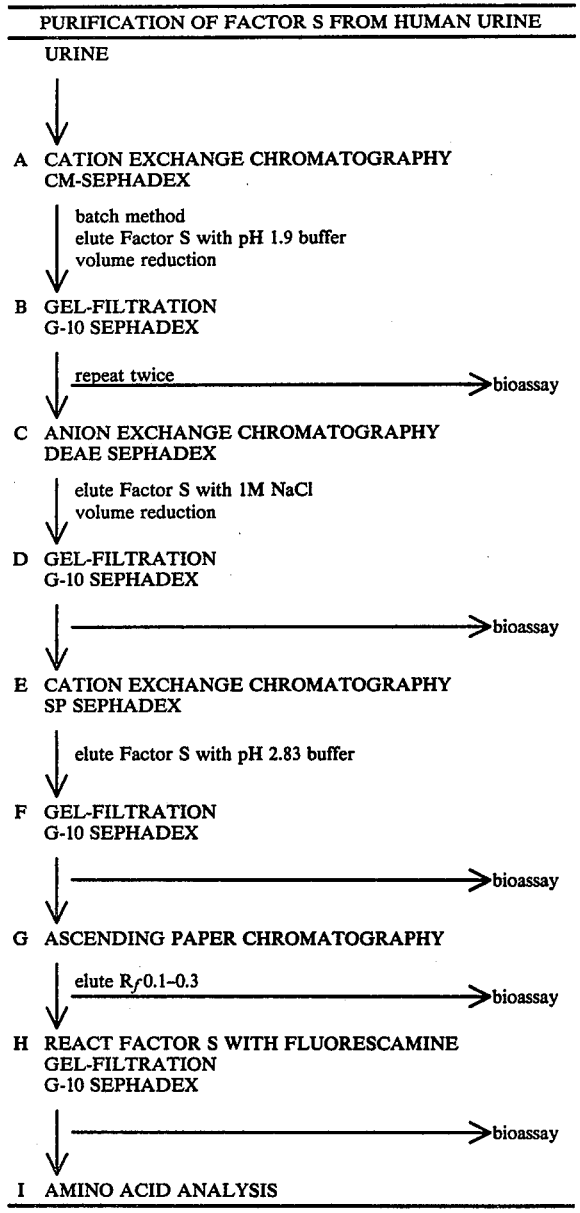

PURIFICATION OF FACTOR S FROM HUMAN URINE

URINE
- A CATION EXCHANGE CHROMATOGRAPHY CM-SEPHADEX
  - batch method
  - elute Factor S with pH 1.9 buffer
  - volume reduction
- B GEL-FILTRATION G-10 SEPHADEX
  - repeat twice → bioassay
- C ANION EXCHANGE CHROMATOGRAPHY DEAE SEPHADEX
  - elute Factor S with 1M NaCl
  - volume reduction
- D GEL-FILTRATION G-10 SEPHADEX
  - → bioassay
- E CATION EXCHANGE CHROMATOGRAPHY SP SEPHADEX
  - elute Factor S with pH 2.83 buffer
- F GEL-FILTRATION G-10 SEPHADEX
  - → bioassay
- G ASCENDING PAPER CHROMATOGRAPHY
  - elute $R_f$ 0.1–0.3 → bioassay
- H REACT FACTOR S WITH FLUORESCAMINE GEL-FILTRATION G-10 SEPHADEX
  - → bioassay
- I AMINO ACID ANALYSIS Step I: Preparation of Urine Samples Human urine was obtained from healthy male adults and frozen within one hour of collection. Prior to starting the purification procedure, the samples were thawed and clarified by centrifugation or filtration.

Step II: Cation Exchange

Cation exchange was carried out using a batch method. A 50 l batch of urine was added to 2.5 l carboxymethyl polysaccharide ((CM) Sephadex C-25), at pH 7, to form a slurry which was stirred with a motorized stirrer for 1 hour. The slurry was allowed to settle, the liquid was decanted, and the remaining slurry was then poured into an empty column. The column was then washed with 1 bed volume of 50 mM $NH_4$ Ac buffer, pH 7, and the wash discarded. The column was then washed again, this time with 1 bed volume of distilled water.

Factor S was then eluted from the column with concentrated HAc—HCOOH at pH 1.9, which treatment converted the cationic form of Factor S to the anionic form. This conversion, which occurs via a mechanism which is not as yet understood, is an important property of Factor S, both from a characterization standpoint—to the best of our knowledge, Factor S is unique in this regard—and from a purification standpoint.

The volume of the eluate was then reduced by lyophilization, and the product was then twice applied to and eluted from a G-10 Sephadex column to remove buffers and other small molecules and then lyophilized.

Step III: Anion Exchange

The change in the charge properties of Factor S permitted the use of an anion exchange resin equilibrated at relatively low pH values to separate the cations originally extracted by CM Sephadex from Factor S which had undergone a charge change.

DEAE Sephadex A-25 was swollen overnight in 500 mN $NH_4$-acetate buffer, pH 5.0. The next day it was washed on a Buchner funnel with at least 10 volumes of 50 mM $NH_4$-acetate buffer, pH 5. The resin was stored at 0° in this buffer until used.

The lyophilized product from the previous step was dissolved in 2 liters of pH 5.0, 50 mM $NH_4$-acetate buffer and applied to a 1 liter bed volume column containing the equilibrated DEAE-Sephadex resin. The column was developed by washing with 1 liter of pH 5.0, 50 mM $NH_4$-acetate buffer followed by 6 liters of 50 mM acetic acid, pH 3.1. Factor S remained bound to the resin and the washes were discarded. A NaCl gradient from 0–1 M NaCl was then used to develop the column, and Factor S was found to elute between 0 and 0.5 M NaCl. The volume of these eluates were then reduced to about 1 liter by low pressure evaporation at 40° in preparation for desalting by gel-filtration on G-10 Sephadex.

Step IV: Cation Exchange

The next state of purification involved the use of a strongly acidic cation exchanger equilibrated and developed at low pH. SP-Sephadex C-25 was swollen overnight in 0.3 M LiOH, pH 11.0 buffer. The slurry was poured into a column of 95 ml bed volume. This column was then washed with Beckman Starting buffer pH 2.2 until the column effluent was pH 2.2. Initially the column was calibrated using cysteic acid, taurine, aspartic acid, and oxidized glutathione as markers. These standards were taken up in 6 ml of the pH 2.2 starting buffer and applied to the column. The column was developed by washing with 30 additional ml of the pH 2.2 buffer followed by continuous washing with Beckman Licitrate buffer, pH 2.83. These conditions allowed the complete separation of these standards from each other. Their peak elution volumes were cysteic acid 61 ml, tau 85 ml, asp 137 ml, and GSSG 195 ml.

The product from the previous step was taken up in 6.0 ml of the pH 2.2 starting buffer and applied to the column. The column was developed as described for the standards. The eluate was fractionated; each fraction was about 8 ml and a total of 250 ml was collected. Under these conditions sleep-promoting activity was found in the 83–91 ml fraction. The volume of this sample was reduced to about 1 ml by lyophilization, then about 2 ml of distilled water were added, and the sample was applied to a G-10 Sephadex column as before.

Step V: Ascending Paper Chromatography

The product from the previous step was lyophilized to near dryness, then a drop was taken up in a Pasteur pipette and placed on Whatman No. 1 paper with a solvent system of acetone:1-propanol:water:8 M NH$_4$OH (40:30:20:10, V:V:V:V). The section of paper between R$_f$ 0.1 and 0.3 was then placed in a test tube with distilled water and allowed to stand. The filter paper was removed and the product contacted with fluorescamine which combined with free amino groups of impurities, while failing to react with Factor S. The mixture was poured through a G-10 column, and Factor S was then recovered in the fraction preceding the standard glucose peak, while the impurities combined with fluorescamine were retarded on the column.

Step VI: Further Characterization

Product from the previous step, when submitted to acid hydrolysis (6 N HCl, 4 hours, 145° C.) yielded alanine, glutamic acid, and diaminopimelic acid (DAP) in the molar ratio 2:2:1, as well as variable amounts of glycine. Milder hydrolysis yielded two amino sugars: muramic acid, equimolar with DAP, and glucosamine, equimolar with glycine.

The biological activity of various fractions correlated well with the amount of DAP, alanine, and glutamic acid released by hydrolysis, and not with the amounts of glycine and glucosamine. Since the molar ratios of glycine and glucosamine are not integers with respect to the other components remaining at the end of step (v), and because biological activity is associated with the other components, we assign, as the composition of Factor S, muramic acid, alanine, DAP, and glu, in the molar ratio 1:2:1:2, glu referring to free glutamic acid after hydrolysis, which may be in the form of glutamine in the unhydrolyzed molecule.

BIOLOGICAL ASSAYS

Biological assays for sleep-promoting activity were performed on rabbits provided with chronically implanted ventricular guide tubes and four epidural screw electrodes for EEG. The animals were allowed two weeks to recover from surgery prior to their use for assays. Samples for testing were taken up in sterile, artificial cerebrospinal fluid and infused intraventricularly at the rate of 3 μl min$^{-1}$ for 90 minutes through a No. 26 hypodermic needle inserted through the guide tube. The recorded infusion pressure was less than 20 cm. H$_2$O, thus providing assurance that the needle was properly placed in the lateral ventricle. Following the infusion the animals were left undisturbed for 6–8 hours while EEG and bodily movements were recorded. Slow wave sleep (SWS) was scored in two ways: (i) by conventional subjective scoring of the duration of SWS from polygraph records and (ii) by digital print-out of integrated mean rectified cortical slow waves ($\frac{1}{2}$–4 Hz), thus obtaining a measure of the amplitude as well as duration of delta wave EEG activity.

The following table shows the result of a typical set of assays designed to determine the effects of enzymatic cleavage with carboxypeptidase.

TABLE

| Number of Rabbits | Infusion Fluid | % SWS 2-6 Hours After Infusion Mean + S.E. |
|---|---|---|
| 4 | None | 42 ± 2 |
| 4 | 90 GBE Factor S + Carboxypeptidases | 46 ± 5 |
| 6 | 90 GBE Factor S | 66 ± 3 |
| 1 | 90 GBE Factor S + Denatured Carboxypeptidase | 64 |

What is claimed is:

1. A process for the preparation of a sleep-promoting factor having the following characteristics:
   (a) it is inactivated by incubation with carboxypeptidase;
   (b) upon elution from a cation exchange resin under acidic conditions the cationic form is converted to the anionic form;
   (c) it has a R$_f$ of 0.15–0.35 after ascending paper chromatography on Whatman No. 1 paper by development with a mixture of acetone:1-propanol:water:8 M NH$_4$OH (40:30:20:10, V/V/V/V);
   (d) it has R$_{LYS}$ of 0.2–0.3 after high voltage electrophoresis at pH 1.9, 65 V cm$^{-1}$ for 60 minutes in formic acid:acetic acid:water (150:100:750, V/V/V) on Whatman No. 3 paper;
   (e) it passes through a molecular sieve which prevents the passage of molecules larger than 1000 daltons;
   (f) it elutes prior to sucrose on a polysaccharide gel-filtration column;

which comprises:
   (i) extraction of homogenized brains from sleep-deprived animals with an acidified organic solvent;
   (ii) ion exchange of the extract from (i) with a cation exchange resin and elution under acidic conditions;
   (iii) removal of buffers and other small molecules by solvent extraction and re-extraction;
   (iv) ion exchange of the extract remaining after Step (iii) with an anion exchange resin; and
   (v) elution of said sleep-promoting factor from said anion exchange resin.

2. The process of claim 1, wherein:
   (i) the acidified organic solvent is a mixture of acetone and aqueous hydrochloric acid; and
   (ii) the cation exchange resin is carboxymethyl polysaccharide.

3. A pure sleep-promoting factor having the following characteristics:
   (a) it is inactivated by incubation with carboxypeptidase;
   (b) it has a R$_f$ of 0.15–0.35 after ascending paper chromatography on Whatman No. 1 paper by development with a mixture of acetone:1-propanol:water:8 M NH$_4$OH (40:30:20:10, V/V/V/V);
   (c) it has R$_{LYS}$ of 0.2–0.3 after high voltage electrophoresis at pH 1.9, 65 V cm$^{-1}$ for 60 minutes in formic acid:acetic acid:water (150:100:750, V/V/V) on Whatman No. 3 paper;
   (d) upon elution from a cation exchange resin under acidic conditions the cationic form is converted to the anionic form;
   (e) it passes through a molecular sieve which prevents the passage of molecules larger than 1000 daltons;
   (f) it elutes prior to sucrose on a polysaccharide gel-filtration column; and (g) it comprises muramic acid, alanine, DAP, and glu, in the molar ratio 1:2:1:2.

4. A sleep-promoting factor isolated from the brains of sleep-deprived animals by the process which comprises:
   (i) extraction of homogenized brains from sleep-deprived animals with an acidified organic solvent;
   (ii) ion exchange of the extract from (i) with a cation exchange resin;
   (iii) removal of buffers and other small molecules;
   (iv) ion exchange of the extract remaining after Step (iii) with an anion exchange resin; and
   (v) elution of said sleep-promoting factor from said anion exchange resin.

5. A sleep-promoting factor as claimed in claim 4 wherein:
   said extraction is carried out on whole brains at 0° to 10° C.;
   said solvent consists essentially of a mixture of a water-soluble ketone with an aqueous mineral acid solution 0.5 to 2 N at a ratio of 20 to 40:1 (V/V); and
   said extract solution is neutralized to about pH 7 before ion exchange.

6. A process for the preparation of a sleep-promoting factor having the following characteristics:
   (a) it has a $R_f$ of 0.15–0.35 after ascending paper chromatography on Whatman No. 1 paper by development with a mixture of acetone:1-propanol:water:8 M $NH_4OH$ (40:30:20:10, V/V/V/V);
   (b) it has $R_{Lys}$ of 0.2–0.3 after high voltage electrophoresis at pH 1.9, 65 V cm$^{-1}$ for 60 minutes in formic acid:acetic acid:water (150:100:750, V/V/V) on Whatman No. 3 paper;
   (c) upon elution from a cation exchange resin under acidic conditions the cationic form is converted to the anionic form;
   (d) it passes through a molecular sieve which prevents the passage of molecules larger than 1000 daltons;
   (e) it elutes prior to sucrose on a polysaccharide gel-filtration column;
   (f) it comprises muramic acid, alanine, DAP, and glu, in the molar ratio 1:2:1:2;
   which comprises:
   (i) ion exchange of human urine with a cation exchange resin and elution under acidic conditions;
   (ii) removal of buffers and other small molecules by chromatography;
   (iii) ion exchange of the extract remaining after Step (ii) with an anion exchange resin;
   (iv) elution of said sleep-promoting factor from said anion exchange resin;
   (v) removal of buffers from said sleep-promoting factor by chromatography;
   (vi) ion exchange of the product remaining after Step (v) with a cation exchange resin;
   (vii) elution of sleep-promoting factor with a buffer;
   (viii) removal of buffers from said sleep-promoting factor by chromatography;
   (ix) subjection of the product remaining after Step (viii) to ascending paper chromatography;
   (x) elution of the fraction between $R_f$ 0.1 and $R_f$ 0.3 by development with a mixture of acetone:1-propanol:water:8 M $NH_4OH$ (40:30:20:10, V/V/V/V);
   (xi) contacting of the product remaining after Step (x) with fluorescamine to remove amino compounds not included in said sleep-promoting factor; and
   (xii) elution of purified sleep-promoting factor.

7. A method of inducing sleep in an animal which comprises the administration to said animal of an effective amount of a sleep-promoting factor having the following characteristics:
   (a) it has a $R_f$ of 0.15–0.35 after ascending paper chromatography on Whatman No. 1 paper by development with a mixture of acetone:1-propanol:water:8 M $NH_4OH$ (40:30:20:10, V/V/V/V);
   (b) it has $R_{Lys}$ of 0.2–0.3 after high voltage electrophoresis at pH 1.9, 65 V cm$^{-1}$ for 60 minutes in ormic acid:acetic acid:water (150:100:750, V/V/V) on Whatman No. 3 paper;
   (c) upon elution from a cation exchange resin under acidic conditions the cationic form is converted to the anionic form;
   (d) it passes through a molecular sieve which prevents the passage of molecules larger than 1000 daltons; and
   (e) it elutes prior to sucrose on a polysaccharide gel-filtration column; and
   (f) it comprises muramic acid, alanine, DAP, and glu, in the molar ratio 1:2:1:2.

* * * * *